April 24, 1962 M. L. MEILLAND Plant Pat. 2,141
ROSE PLANT
Filed March 28, 1961
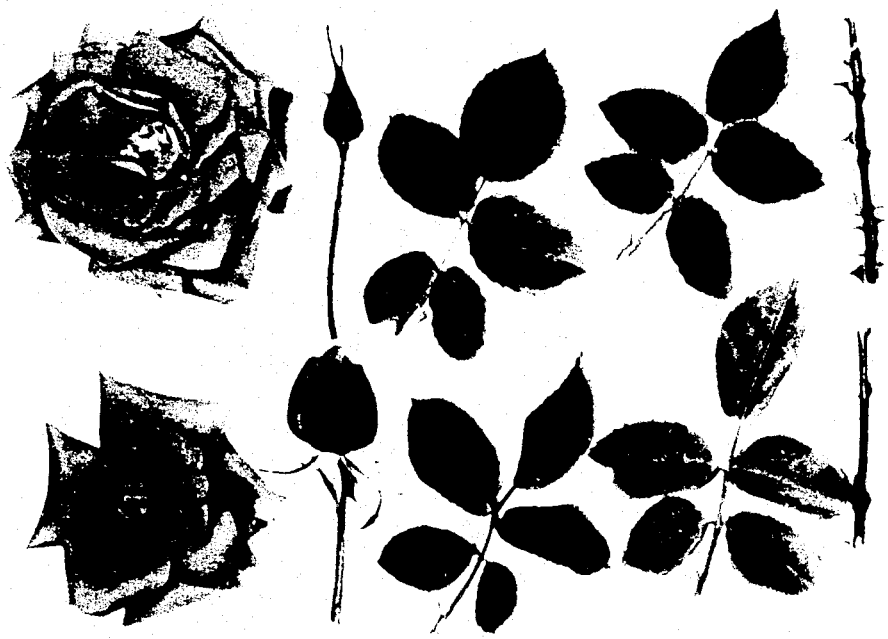
Inventor
Marie Louise Meilland
By: Robb & Robb
Attorneys.

United States Patent Office

Plant Pat. 2,141
Patented Apr. 24, 1962

2,141
ROSE PLANT

Marie Louise Meilland, Alpes Maritimes, France, assignor to The Conard-Pyle Company, West Grove, Pa., a corporation of Pennsylvania Filed Mar. 28, 1961, Ser. No. 98,995
1 Claim. (Cl. 47—61)

The present invention relates to a new and distinct variety of rose plant of the hybrid tea class, which was originated by me by crossing the variety "Monte Carlo" (unpatented) with the variety "Radar" (unpatented).

The primary objective of this breeding was to produce a new rose variety which combines the Geranium Red flower color and excellent bloom form of the parent variety "Radar" with the strong plant habit and glossy clean foliage of the parent variety "Monte Carlo." This objective was fully achieved, along with other desirable improvements, as evidenced by the following unique combination of characteristics which are outstanding in the new variety and which distinguish it from its parents, as well as from all other varieties of which I am aware:

(1) A vigorous and well-branched habit of growth;

(2) Distinctive, large, glossy foliage;

(3) Well-formed, high-centered, large blooms usually ranging in size from 4½ inches to 5 inches in diameter; and (4) A distinctive general color tonality of the blooms ranging from Vermilion to Orange Scarlet.

Asexual reproduction of the new variety by budding, as performed at West Grove, Pennsylvania, U.S.A., and also in France, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Color Chart of the Royal Horticultural Society, except where general color terms of ordinary dictionary significance are obvious:

Type: Hardy; bush; outdoor; seedling; for cut flowers and for garden decoration.
Class: Hybrid tea.
Breeding: Seedling.
*Seed parent.*—"Monte Carlo."
*Pollen parent.*—"Radar."
Propagation: Holds its distinguishing characteristics through succeeding propagations by budding.

*Flower*

Locality where grown and observed: West Grove, Pennsylvania, U.S.A.
Flowers borne: Singly to stem; on stems of from medium length to long and from normal strength to strong.
Quantity of bloom: Abundant, outdoors.
Continuity: Continuous.
Fragrance: Moderate. Nature—tea.
Bud:
*Peduncle.*—Medium length; medium caliper; erect; rough; with medium number of hairs having the color of Egyptian Buff, Plate 407/2, lightly overlaid with Garnet Brown, Plate 00918/3. Color—slightly darker than Lettuce Green, Plate 861.
*Before calyx breaks.*—Size—medium. Form—pointed; ovoid; with foliaceous appendages on the surface of the bud; with bristle-like foliaceous parts extending beyond the tip of the bud equal to ¼ of its length.

*As calyx breaks.*—Color—Indian Lake, Plate 826.
*As first petal opens.*—Size—medium. Form—globular. Color: outside—Cardinal Red, Plate 822/2; inside—between Vermilion, Plate 18 and Vermilion, Plate 18/1.
*Opening.*—Opens up well.
Bloom:
*Size (when fully open).*—Large; from 4½ inches to 5 inches.
*Petalage.*—Double; from 30 to 35 petals; arranged regularly.
*Form.*—High-centered at first and remaining high-centered; petals being at first loosely rolled outward, but later becoming tightly rolled outward at maturity.
Petals: Leathery; with both inside and outside satiny. Shape: outer—round; intermediate—round; inner—roundly obovate.

This description of a newly opened flower was made from a rose grown outdoors in the month of August at West Grove, Pennsylvania, U.S.A.;

*Color.*—Outer petal: outside surface—Carmine, Plate 21/1 with occasional veins of Rose Bengal, Plate 25/1; inside surface—Scarlet, Plate 19/1 over upper half of petal, grading to Vermilion, Plate 18/1. Intermediate petal: outside surface—Carmine, Plate 21/1 with occasional veins of Rose Bengal, Plate 25/1; inside surface—Vermilion, Plate 18/1, margined by Scarlet, Plate 19/1. Inner petal: outside surface—Carmine, Plate 21/1; inside surface—between Vermilion, Plate 18 and Vermilion, Plate 18/1.

This description was made from a rose that was open for 3 days outdoors in the month of August at West Grove, Pennsylvania, U.S.A.:

*Color.*—Outer petal: outside surface—Crimson, Plate 22, grading to Currant Red, Plate 821/3 at margin of basal part of petal; inside surface—Scarlet, Plate 19/1, with upper half of petal overlaid with Carmine, Plate 21/1. Inner petal: outside surface—Crimson, Plate 22 at apical margin, grading to Currant Red, Plate 821/3; inside surface—between Scarlet, Plate 19/1 and Scarlet, Plate 19/2, grading to Vermilion, Plate 18/1 over lower half of petal.
*General color effect.*—Newly opened flower—Vermilion, Plate 18/1. 3-days open—between Vermilion, Plate 18/1 and Scarlet, Plate 19/1.
*Behavior.*—Drop off cleanly.
*Flower longevity.*—On bush in garden—4 days in August. Cut flowers grown outdoors and kept at living room temperatures—5 days in August.

*Reproductive Organs*

Stamens: From few to medium number; arranged irregularly about pistils.
Filaments: From medium length to long; most with anthers. Color—Brick Red, Plate 016/1, becoming Sulphur Yellow, Plate 1/2, at base.
Anthers: Medium size; open at various times; occasionally an anther fused with a petaloid. Color—Sulphur Yellow, Plate 1/3.
Pollen: Moderate abundance. Color—Aureolin, Plate 3/1.
Pistils: Medium number.
Styles: Uneven; medium length; thin; bunched.
Stigma: Color—Canary Yellow, Plate 2/2.
Ovaries: All protruding from receptacle.
Hips: None observed.
Sepals: Permanent; moderately long; curled.
Seeds: None observed.

*Plant*

Foliage:

*Leaves.*—Mostly compound of 5 leaflets; normal abundance; moderately large; leathery; glossy.

*Leaflets.*—Shape—oval, with apex acute. Base—obtuse. Margin—simply serrate.

*Color.*—Mature: upper surface—Spinach Green, Plate 0960; under surface—Lavender Green, Plate 000761. Young: upper surface—Fern Green, Plate 0862/1, lightly overlaid with Oxblood Red, Plate 00823/3, and with veins and margin of leaf Oxblood Red, Plate 00823/3; under surface—Sage Green, Plate 000861, lightly overlaid with Oxblood Red, Plate 00823/3, and with veins and midrib of Oxblood Red, Plate 00823/3.

*Rachis (the supporting stem of the compound leaf).*—Medium caliper. Upper side—grooved; hairy. Under side—sparsely hairy; prickly.

*Stipules.*—Medium length; narrow; with points of medium length turning out at an angle of approximately 45°.

*Disease resistance.*—Comparable to that of the average variety grown under the same cultural conditions at West Grove, Pennsylvania, U.S.A., except that it is apparently slightly more susceptible to mildew.

Growth:

*Habit.*—Bushy; upright; much-branched.

*Growth.*—Free.

*Canes.*—Medium caliper.

*Main stems.*—Dull. Color—Spinach Green, Plate 0960/1. Prickles—many; color—slightly lighter than Garnet Brown, Plate 00918/3. Hairs—none.

*Branches.*—Dull. Color—Spinach Green, Plate 0960/1. Prickles—many; color—Fern Green, Plate 0862/3, overlaid with Oxblood Red, Plate 00823/3 at base. Hairs—none.

*New shoots.*—Bright. Color—Spinach Green, Plate 0960/3. Prickles—many; color—Fern Green, Plate 0862/3, overlaid with Oxblood Red, Plate 00823/3. Hairs—none.

I claim:

A new and distinct variety of rose plant of the hybrid tea class, substantially as herein shown and described, characterized particularly as to novelty by the unique combination of a vigorous and well-branched habit of growth distinctive, large and glossy foliage, large, well-formed and high-centered blooms, and a distinctive and attractive general color tonality of the blooms ranging from Vermilion to Orange Scarlet.

No references cited.